(12) United States Patent
Nason

(10) Patent No.: US 9,232,940 B2
(45) Date of Patent: Jan. 12, 2016

(54) METHODS FOR REPAIRING SOFT TISSUE USING ARTHROSCOPIC SUTURE PASSING DEVICES

(71) Applicant: Kevin S. Nason, Chandler, AZ (US)

(72) Inventor: Kevin S. Nason, Chandler, AZ (US)

(73) Assignee: Cayenne Medical, Inc., San Clemente, CA (US)

( * ) Notice: Subject to any disclaimer, the term of this patent is extended or adjusted under 35 U.S.C. 154(b) by 360 days.

(21) Appl. No.: 13/794,180

(22) Filed: Mar. 11, 2013

(65) Prior Publication Data

US 2013/0190782 A1 Jul. 25, 2013

Related U.S. Application Data

(62) Division of application No. 12/604,190, filed on Oct. 22, 2009, now Pat. No. 8,394,112.

(60) Provisional application No. 61/107,637, filed on Oct. 22, 2008.

(51) Int. Cl.
*A61B 17/04* (2006.01)
*A61B 17/062* (2006.01)
*A61B 17/06* (2006.01)

(52) U.S. Cl.
CPC ......... *A61B 17/0469* (2013.01); *A61B 17/0625* (2013.01); *A61B 17/0482* (2013.01); *A61B 2017/0472* (2013.01);
(Continued)

(58) Field of Classification Search
CPC ........... A61B 17/0469; A61B 17/0482; A61B 17/0483; A61B 2017/047; A61B 2017/0472; A61B 2017/06009; A61B 2017/06104

USPC .................. 606/144–148, 139, 232, 224–227
See application file for complete search history.

(56) References Cited

U.S. PATENT DOCUMENTS

| 3,946,740 A | 3/1976 | Bassett |
| 4,164,225 A | 8/1979 | Johnson et al. |

(Continued)

FOREIGN PATENT DOCUMENTS

| DE | WO 2010/019973 | * | 2/2010 | ............. A61B 17/04 |
| WO | 9627331 A1 | | 9/1996 | |

(Continued)

OTHER PUBLICATIONS

Bradley et al. "Arthroscopic Treatment of Multidirectional Instability: Thermal Technique" in "Shoulder Arthroscopy" (edited by Tibone et al., Aug. 2003).

*Primary Examiner* — Todd E Manahan
*Assistant Examiner* — Majid Jamialahmadi
(74) *Attorney, Agent, or Firm* — Donald E. Stout; Stout, Uxa & Buyan, LLP

(57) ABSTRACT

A system for transdermal repair of soft tissue includes an instrument comprising a proximal actuator portion, a fixed needle having a lumen and extending distally from the proximal actuator portion, and a movable needle having a lumen and extending distally from the proximal actuator portion. The movable needle is movable axially between an advanced position and a retracted position relative to the proximal actuator portion. A suture needle is disposed within the lumen of one of the fixed and movable needles, and has a length of suture connected thereto. Needle graspers are disposed in the lumen of each needle, for securing the suture needle and assisting in the transfer of the suture needle from one needle to the other to complete a suture passing step.

8 Claims, 4 Drawing Sheets

(52) U.S. Cl.
CPC .................. *A61B 2017/0608* (2013.01); *A61B 2017/06009* (2013.01); *A61B 2017/0609* (2013.01); *A61B 2017/06042* (2013.01); *A61B 2017/06052* (2013.01); *A61B 2017/06104* (2013.01)

(56) References Cited

U.S. PATENT DOCUMENTS

| | | | |
|---|---|---|---|
| 4,901,721 | A | 2/1990 | Hakki |
| 4,935,027 | A | 6/1990 | Yoon |
| 5,015,249 | A | 5/1991 | Nakao et al. |
| 5,336,231 | A | 8/1994 | Adair |
| 5,403,326 | A | 4/1995 | Harrison et al. |
| 5,431,666 | A | 7/1995 | Sauer et al. |
| 5,665,096 | A * | 9/1997 | Yoon .............................. 606/139 |
| 6,443,963 | B1 * | 9/2002 | Baldwin et al. ................ 606/148 |
| 6,533,795 | B1 | 3/2003 | Tran et al. |
| 6,551,330 | B1 | 4/2003 | Bain et al. |
| 6,618,626 | B2 | 9/2003 | West et al. |
| 6,638,286 | B1 | 10/2003 | Burbank et al. |
| 6,770,084 | B1 | 8/2004 | Bain et al. |
| 6,893,448 | B2 | 5/2005 | O'Quinn et al. |
| 6,921,361 | B2 | 7/2005 | Suzuki et al. |
| 7,063,715 | B2 | 6/2006 | Onuki et al. |
| 7,087,064 | B1 | 8/2006 | Hyde |
| 7,112,208 | B2 | 9/2006 | Morris et al. |
| 7,118,583 | B2 | 10/2006 | O'Quinn et al. |
| 7,166,116 | B2 | 1/2007 | Lizardi et al. |
| 7,232,446 | B1 | 6/2007 | Farris |
| 7,513,904 | B2 | 4/2009 | Sulamanidze et al. |
| 7,918,868 | B2 | 4/2011 | Marshall et al. |
| 8,177,795 | B2 | 5/2012 | Niese et al. |
| 8,267,948 | B2 | 9/2012 | Marshall et al. |
| 2002/0095199 | A1 | 7/2002 | West et al. |
| 2002/0128533 | A1 | 9/2002 | Barker |
| 2003/0078599 | A1 | 4/2003 | O'Quinn et al. |
| 2003/0083695 | A1 | 5/2003 | Morris et al. |
| 2003/0236535 | A1 | 12/2003 | Onuki et al. |
| 2004/0034371 | A1 | 2/2004 | Lehman et al. |
| 2004/0059352 | A1 | 3/2004 | Burbank et al. |
| 2004/0092968 | A1 | 5/2004 | Caro et al. |
| 2004/0260314 | A1 | 12/2004 | Lizardi et al. |
| 2008/0077162 | A1 | 3/2008 | Domingo |
| 2010/0113873 | A1 | 5/2010 | Suzuki et al. |
| 2010/0114123 | A1 | 5/2010 | Nason |
| 2010/0280530 | A1 | 11/2010 | Hashiba |
| 2011/0118757 | A1 | 5/2011 | Pierce |
| 2011/0144666 | A1 * | 6/2011 | Egle et al. ..................... 606/144 |
| 2013/0274769 | A1 * | 10/2013 | Bonutti et al. ................. 606/148 |

FOREIGN PATENT DOCUMENTS

| | | |
|---|---|---|
| WO | 9903402 A1 | 1/1999 |
| WO | 0189370 A2 | 11/2001 |
| WO | 2008113076 A2 | 9/2008 |
| WO | 2009005527 A1 | 1/2009 |

* cited by examiner

METHODS FOR REPAIRING SOFT TISSUE USING ARTHROSCOPIC SUTURE PASSING DEVICES This U.S. Utility Patent Application is a divisional application under 35 U.S.C. 120 of commonly assigned U.S. patent application Ser. No. 12/604,190 entitled Arthroscopic Suture Passin Devices and Methods filed Oct. 22, 2009, and issuing on Mar. 12, 2013 as U.S. Pat. No. 8,394,112, which in turn claims the benefit under 35 U.S.C. 119(e) of the filing date of U.S. Provisional Patent Application Ser. No. 61/107,637, entitled Arthroscopic Suture Passing Device, filed on Oct. 22, 2008, the contents of each of which are expressly incorporated herein by reference in their entirety.

BACKGROUND OF THE INVENTION

This invention relates generally to methods and apparatus for repairing soft tissue arthroscopically, and more particularly to methods and apparatus for passing suture through soft tissue.

There are many procedures, such as capsular plication, Bankart lesion repairs, or reconstruction of labral tissue to the glenoid rim, in which a practitioner needs to secure tissue in close contact with bone. Suture is passed through soft tissue, the bone surface is roughened, and when tissue is pulled into intimate contact, the body's healing response will fuse the tissue and bone together.

Such procedures are often accomplished by implanting an anchor, pre-loaded with a strand of suture, into a hole drilled in the bone at a desired anchor location. One or both of the suture ends are then passed through soft tissue at the desired location, the tissue is pulled close to the bone at the anchor site, and the suture is secured to the anchor by tying a knot.

There are many suture passing devices on the market today, which are intended to pass suture through soft tissue. Some are designed for specific locations—i.e. devices like the Arthrex VIPER and SCORPION, which are designed to grasp rotator cuff tissue and pass a suture perpendicularly through it. Using these types of devices, the surgeon captures the edge of the tissue in the jaws of a grasper, which stabs a needle, carrying suture, through the rotator cuff tissue. The suture is then retrieved with a grasper. However, this device cannot pass suture multiple times without reloading the device. Also, since they are optimized for rotator cuff tissue, they cannot reach many of the areas within the gleno-humeral joint space.

More general suture passer designs consist of a needle bent into several curved shapes at the sharp end. The curves differ in angle of bend, direction of curve, and shape of curve, to allow the surgeon to reach as many locations within the joint as possible. The surgeon plunges the tip of the needle into tissue at one location and back out of the tissue at another. Suture is then "shuttled" through the needle. The needle is removed and the suture remains, passing through the tissue at the desired location.

The Conmed Linvatec Spectrum suture passing device is a general purpose suture passing device that comes with several different suture hook variations to allow for access to multiple locations within the joint. This device can use monofilament suture for shuttling or a dedicated suture lasso. In an effort to eliminate suture shuttling, Conmed has recently released the Spectrum MVP product. This device adds a tube which runs alongside the curved needle. The curved needle is passed through the tissue. A nitinol suture snare is then deployed from inside the tip of the curved needle, which opens to form a loop. A piece of suture, which is loaded onto the tip of the straight tube, is pushed forward and through the loop by a nitinol push-rod. The snare is closed around the suture and push-rod, capturing the suture. The curved needle is then pulled back through the tissue, bringing the suture along with it and out of the joint. Although this new device eliminates the shuttling step, it must be passed completely through the tissue (in order to deploy the nitinol snare) and it can only make one suture pass at a time. It must be removed from the joint and reloaded with suture for each pass. Also, if the joint space is small, the nitinol loop may not be able to fully open or may get pushed to the side. In this case, it may no longer line up with the nitinol push-rod and be able to capture the suture.

There are several methods of "shuttling" suture once the needle is passed through the tissue. Since it is difficult to push suture down the long needle, often a "suture shuttle" is passed down the shaft and out the end of the needle where it is grasped by an arthroscopic grasper, often introduced into the joint space through another portal. One end of the suture shuttle is pulled out of the joint space, attached to a free end of the suture that will remain in the body, then pulled back through the tissue. This pulls the suture back through the hole, where it is then used to secure the tissue to the desired location, often an anchor. Common suture shuttles are monofilament suture (which is tied around the high-strength suture to pull it back through the tissue), monofilament suture loops to snare the suture, or dedicated snares made of nitinol wire.

One of the most difficult steps in passing suture through soft tissue with existing devices is piercing the needle completely through the tissue. Piercing the needle tip into the tissue is usually not difficult. However, getting the tip of the needle back out of the tissue so that the suture shuttle can be passed out of the end can be difficult, especially if the tissue is very soft. This is often the case in the inferior capsule of the shoulder. An important step in reducing laxity of the shoulder, called capsular plication or capsular shift, is passing suture through capsular tissue inferior to the glenoid. This tissue is often very soft and does not provide enough tension to resist the needle and allow the tip to pierce back out of the tissue.

Arthrex, TAG, and several other companies also make suture passers which operate slightly differently, and do not require suture shuttling. Arthrex's version, the Birdbeak, resembles a sharply pointed set of suture graspers. The device is pierced through the tissue, grasps suture already in the joint space (usually attached to an anchor), and pulls the suture back through the tissue. These devices do not require suture shuttling and can, theoretically, pull sutures through different locations without removing the device from the joint space. However, mobility of the device is severely limited once it has been pierced through the tissue. This requires the suture to be in the correct location to be grasped. This is often accomplished by holding and manipulating the suture with a grasper placed into the joint through a second working portal.

SUMMARY OF THE INVENTION

The invention described and shown herein is intended to make passing suture through soft tissue easier for a practitioner. The devices currently used for this type of procedure are generally called suture passing devices or suture passers. The new device of the invention addresses multiple issue present in currently marketed devices. The new device does not require the suture passer to be completely passed through (into or out of) the tissue, does not require suture shuttling, has the ability to pass suture multiple times through tissue without removing the device from the joint space or reloading suture, and operates through a single arthroscopic working portal. Practitioners using the systems and methods of this invention do not need to bring the tip of the needle back out of the tissue in order to pass suture. By using two needles which meet at the tips, the surgeon simply pierces the curved needle tip into the tissue, advances the second needle—which meets up with the tip of the curved needle—and passes suture between them. This eliminates the most technically difficult parts of the prior art procedures.

Another improvement over currently marketed devices is the elimination of suture shuttling. Suture shuttling is a very tedious process which takes a great deal of time during the procedure. As stated previously, the tip of the needle must pierce into and completely out of the tissue in order to push the suture shuttle out of the tip. Even if there is a small film of tissue over the hole in the end of the needle, the suture shuttle will not pass through. Also, the practitioner must grasp the end of the suture shuttle and pull it out of the joint space. With many sutures in the way and a tight joint space, this can be challenging. Problems can occur when pulling the suture back through the hole in the tissue. Monofilament suture, often tied with a knot around the suture, can break, or the knot can untie when pulling the suture back through the tissue. This often requires the entire suture passing procedure to be repeated. Suture can slip out of monofilament loops, and dedicated nitinol snares are expensive. Finally, suture shuttling takes considerable operating room time. A common Bankart repair utilizing three anchors, each with a mattress stitch through nearby tissue, requires six separate suture shuttling procedures. This can easily take 10 or 12 minutes of a 30-40 minute surgery.

Yet another time consuming step with existing devices and methods involves removing and re-inserting the device into the joint space with each suture shuttle step. After the shuttle is passed through the tissue, the suture passing device is removed from the joint space, the suture is shuttled, and the device re-inserted for the next suture pass. This new device can make multiple suture passes through the tissue without shuttling suture or removing the device between each one. During a shoulder plication, this allows the surgeon to quickly make multiple pleats in the tissue to optimize the direction and amount of capsular tightening—something that would be very difficult and time consuming with existing approaches.

Additionally, the inventive system can pass suture multiple times through a single cannula. Many of the other devices in the prior art require (or are helped considerably by) a grasper or other suture manipulating instrument in the joint space. Using multiple devices simultaneously requires more than one working portal. By using a single portal approach, the practitioner may be able to make the surgical procedure considerably less invasive for the patient.

More particularly, there is provided a system for transdermal repair of soft tissue, which includes an instrument comprising a proximal actuator portion, a fixed needle having a lumen and extending distally from the proximal actuator portion, and a movable needle having a lumen and extending distally from the proximal actuator portion. The movable needle is movable axially between an advanced position and a retracted position relative to the proximal actuator portion. A suture needle is disposed within the lumen of one of the fixed and movable needles, and has a length of suture connected thereto. A needle grasper is disposed in the lumen of the aforementioned one of the fixed and movable needles, proximally of the suture needle, and has grasper jaws disposed on a distal end thereof which are movable between a closed orientation and an open orientation. The grasper jaws are adapted for securing a first end of the suture needle.

A second needle grasper is disposed in the lumen of the other of the fixed and movable needles, and has grasper jaws disposed on a distal end thereof which are movable between a closed orientation and an open orientation. The grasper jaws on the second needle grasper are adapted for securing a second end of the suture needle.

Preferably, the suture needle comprises a flexible wire having a first collar disposed at the first end and a second collar disposed at the second end. The collars provide a means for the grasper jaws of each of the needle graspers to readily engage the suture needle ends. A coil on the suture needle is slidable therealong, and the length of suture is connected to the coil.

In the preferred embodiment, the fixed needle is curved at a distal end thereof, and the movable needle is straight.

An actuator is provided on the actuator portion for axially moving the movable needle. A second actuator on the actuator portion functions to move the suture needle between the movable needle and the fixed needle.

To actuate the grasper jaws on each grasper between their open and closed orientations, the lumen in the aforementioned one of the fixed and movable needles has a smaller diameter portion and a larger diameter portion, with the larger diameter portion being distal to the smaller diameter portion, so that as the needle grasper moves distally within the lumen of that needle, it moves from the smaller diameter portion, wherein the grasper jaws are forced into their closed orientation to clamp the first end of the suture needle in place, to the larger diameter portion, at which time the grasper jaws move to their open orientation to release the first end of the suture needle. Similarly, the lumen in the other of the fixed and movable needles has a smaller diameter portion and a larger diameter portion, the larger diameter portion being distal to the smaller diameter portion, so that as the second needle grasper moves proximally within the lumen of the other of the fixed and movable needles, it moves from the larger diameter portion, wherein the grasper jaws are released into their open orientation, to the smaller diameter portion, at which time the second grasper jaws are forced into their closed orientation to clamp the second end of the suture needle in place. The needle graspers are movable, respectively, relative to the needle in which they are disposed and within the lumen of that needle.

In another aspect of the invention, there is provided a system for transdermal repair of soft tissue, which includes an instrument comprising a proximal actuator portion, a curved needle having a lumen and extending distally from the proximal actuator portion, and a movable straight needle having a lumen and extending distally from the proximal actuator portion, wherein the movable needle is movable axially between an advanced position and a retracted position relative to the proximal actuator portion. A suture needle is disposed within the lumen of one of the straight and curved needles, and has a length of suture connected thereto. A needle grasper is disposed in the lumen of the aforementioned one of the straight and curved needles, proximally of the suture needle, and has grasper jaws disposed on a distal end thereof which are movable between a closed orientation and an open orientation. The grasper jaws are adapted for securing a first end of the suture needle, and the needle grasper is axially movable within the lumen of the one of the straight and curved needles, relative to that needle. A second needle grasper is disposed in the lumen of the other of the straight and curved needles and has grasper jaws disposed on a distal end thereof which are movable between a closed orientation and an open orientation. The second needle grasper jaws are adapted for securing a second end of the suture needle. The second needle grasper is axially movable within the lumen of the other of the straight and curved needles, relative to that needle.

The suture needle preferably comprises a flexible wire having a first collar disposed at the first end and a second collar disposed at the second end. The grasper jaws of each of the needle graspers may readily engage the collars to secure the suture needle. A coil is provided on the suture needle which is slidable therealong, wherein the length of suture is connected to the coil. An actuator on the actuator portion axially moves the movable straight needle, and a second actuator on the actuator portion moves the suture needle between the movable straight needle and the curved needle.

To actuate the grasper jaws on each grasper between their open and closed orientations, the lumen in each of the straight and curved needles has a smaller diameter portion and a larger diameter portion, the larger diameter portion being distal to the smaller diameter portion. With this construction, as the needle grasper in each respective needle moves distally within the lumen of that needle, it moves from the smaller diameter portion, wherein the grasper jaws are forced into their closed orientation to clamp one of the ends of the suture needle in place, to the larger diameter portion, at which time the grasper jaws move to their open orientation to release that suture needle end. As the needle grasper in each respective needle moves proximally within the lumen of that needle, it moves from the larger diameter portion, wherein the grasper jaws are released into their open orientation, to the smaller diameter portion, at which time the grasper jaws are forced into their closed orientation to clamp the suture needle end in place.

In still another aspect of the invention, there is disclosed a method of repairing soft tissue, which comprises steps of introducing an instrument having a curved needle and a movable straight needle, each extending distally from a proximal actuator portion, into an operative site, piercing tissue to be sutured with a distal end of the curved needle, and advancing the straight needle until a distal end thereof lines up with and meets the distal end of the curved needle. A suture needle, disposed in one of the curved and movable straight needles, is then passed from one of the curved and movable straight needles to the other one of those needles. The movable straight needle is then retracted proximally, and the curved needle is pulled back through the tissue, thereby creating a stitch of suture in the tissue.

In the above described method, the suture needle is initially clamped on one end by a grasper disposed in the aforementioned one of the curved and movable straight needles, and the passing step comprises moving the grasper distally to push the suture needle out of the one of the curved and movable straight needles and into the other of the curved and movable straight needles. The passing step further comprises releasing the one end of the suture needle from the grasper and clamping the other end of the suture needle using a second grasper disposed in the other of the curved and movable straight needles.

The invention, together with additional features and advantages thereof, may best be understood by reference to the following description taken in conjunction with the accompanying illustrative drawing.

DESCRIPTION OF THE PREFERRED EMBODIMENT

Figure 1:
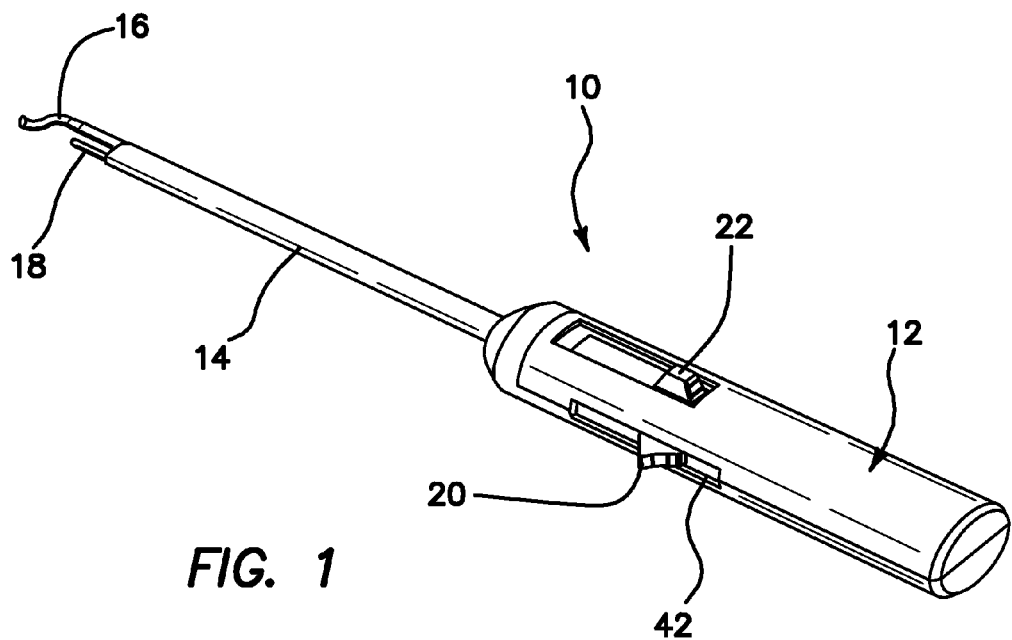
FIG. 1 is an isometric view of a suture passing device constructed in accordance with the principles of the present invention.

Referring now more particularly to the drawings, there is shown in FIG. 1 a suture passing device 10 which is constructed in accordance with the principles of the present invention. The device 10 is a simple suture passing device which does not require suture shuttling, has the ability to pass suture multiple times through tissue without removing the device from the joint space or re-loading suture, and operates through a single working portal.

The device 10 comprises a proximal actuator portion or handle 12 and a distal sheath 14. Within and extending distally of the sheath 14 are a curved needle 16 and a movable straight needle 18. The handle 12 includes a straight needle slider 20 and a suture slider 22, the functions of which will be described below.

Figure 6:
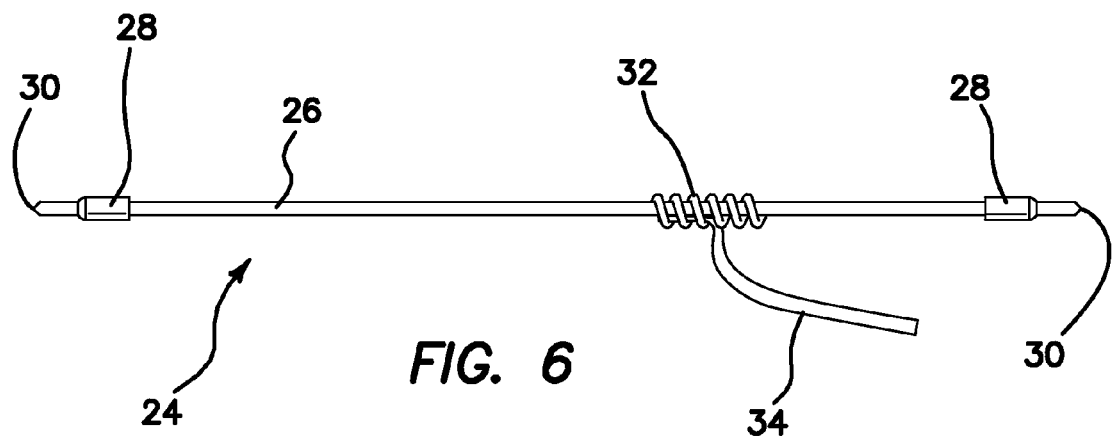
FIG. 6 is a plan view of the suture needle of the invention.

A suture needle 24 for use in the inventive device 10 is illustrated in FIG. 6. The suture needle 24 comprises a length of flexible wire 26, preferably nitinol, having a collar 28 disposed on each end. Each end 30 of the wire 26 is sharpened to allow it to easily pierce tissue. There is also a coil 32 wrapped around the wire 26, which secures a length of suture 34.

Figure 7:
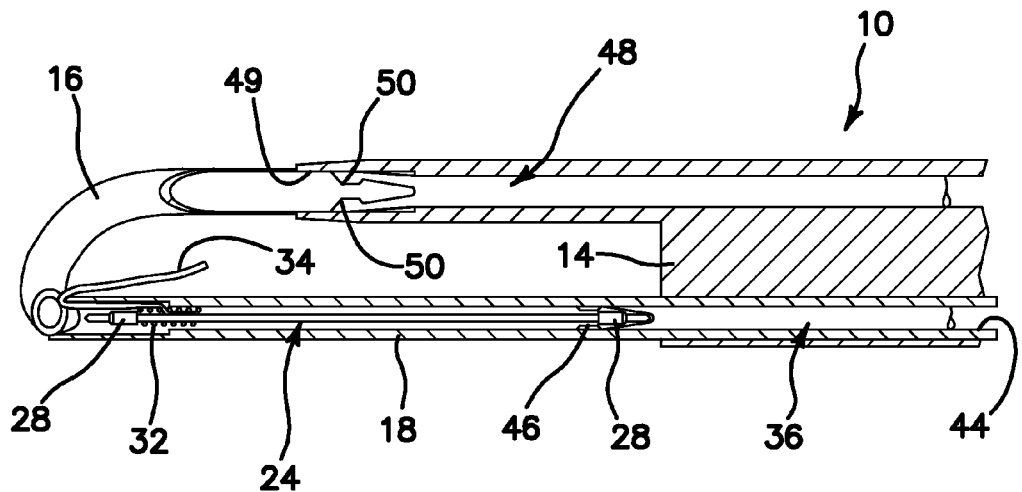
FIG. 7 is a detailed view illustrating the suture needle passing system of the invention prior to passing of the suture needle.
Figure 8:
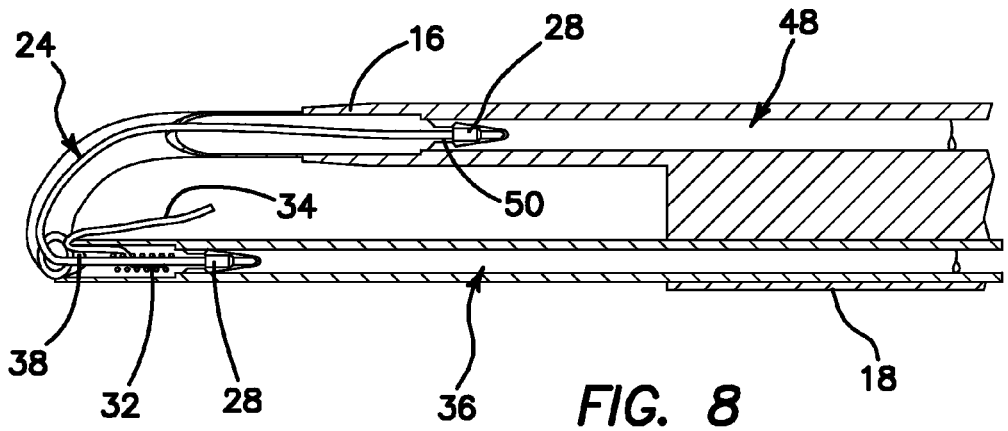
FIG. 8 is a detailed view similar to FIG. 7, wherein the suture needle is passing through the tissue.
Figure 9:
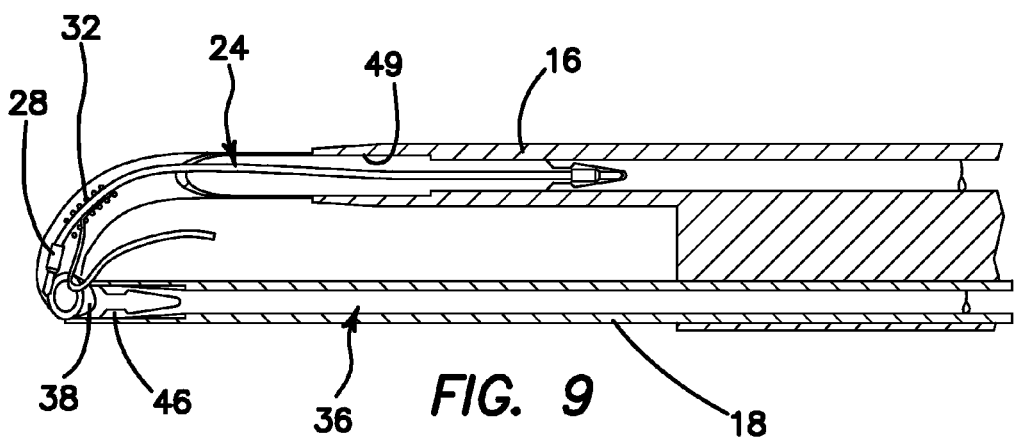
FIG. 9 is a detailed view similar to FIGS. 7 and 8, wherein the suture needle has been passed through the tissue.

Referencing FIGS. 7-9, which illustrate the suture needle passing system, it can be seen that the inventive system further comprises a needle grasper 36.

Figure 2:
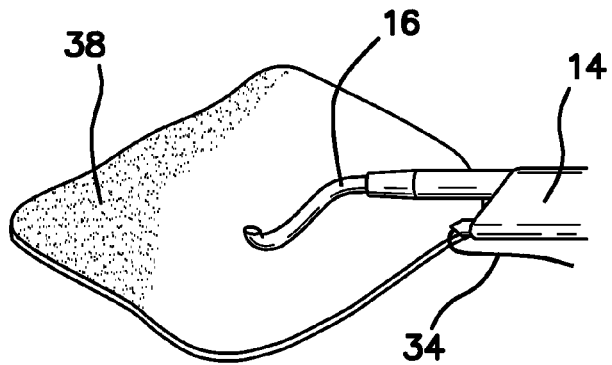
FIG. 2 is an isometric view illustrating the distal end of the device of FIG. 1, as the tissue to be repaired is pierced by the curved needle of the device.
Figure 3:
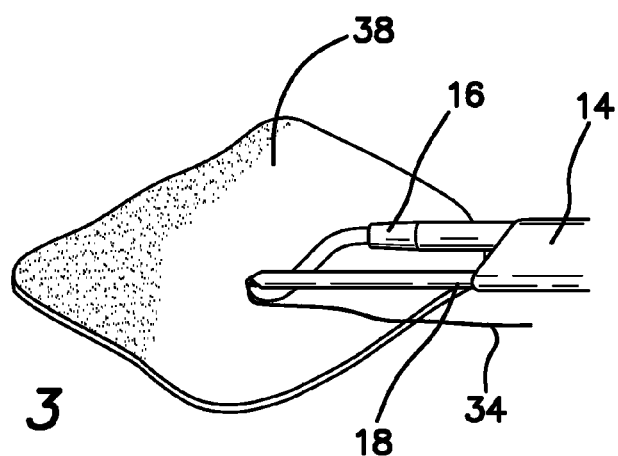
FIG. 3 is an isometric view similar to FIG. 2, wherein the straight needle of the device has been advanced to meet the curved needle.

A procedure for passing suture using the device 10 will now be described. To begin the procedure, the practitioner holds and manipulates the handle 12. The passing end, or distal end of the device 10, as noted above, comprises the curved needle 16 and the movable straight needle 18. The practitioner receives the device 10 with suture pre-loaded into the straight needle 18. The tip of the device is passed through a cannula (not shown) into the joint space, which comprises the procedural site. As shown in FIG. 2, the practitioner pierces tissue 38 with the curved needle 16 in a suture exit location 40 where one end of the suture 34 will emerge. The curved tip of the device may be brought back out of the tissue or left underneath. The device is manipulated so the location of suture exit 40 is lined up with the straight needle 18. The straight needle is then advanced until it stops, at which point the tip of the straight needle lines up with and meets the tip of the curved needle, as shown in FIG. 3. The straight needle 18 may completely pierce tissue, but there may also be a layer of tissue captured between the tips of the two needles.

Figure 4:
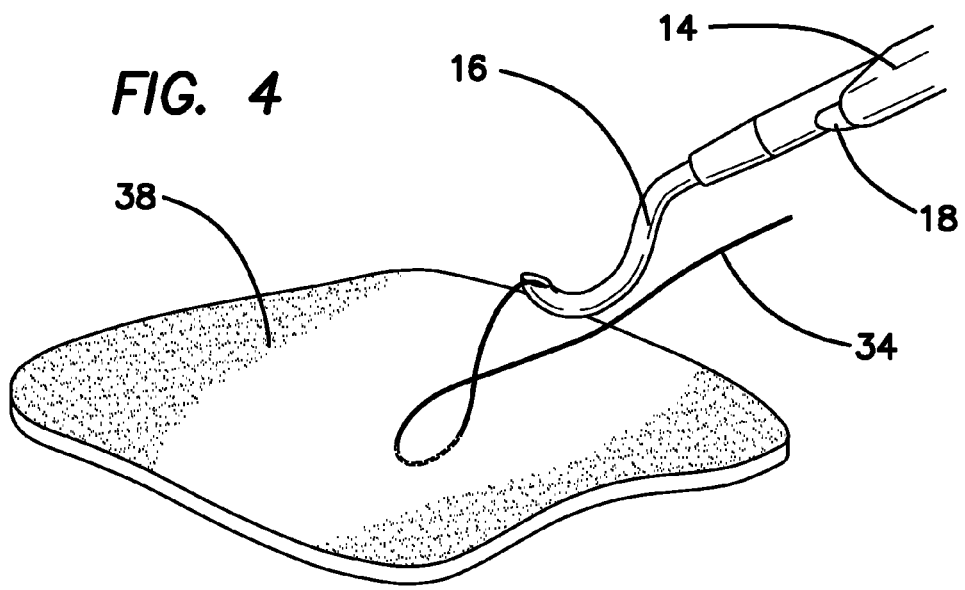
FIG. 4 is an isometric view similar to FIGS. 2 and 3, wherein the curved needle has been removed from the tissue after the first suture pass.
Figure 5:
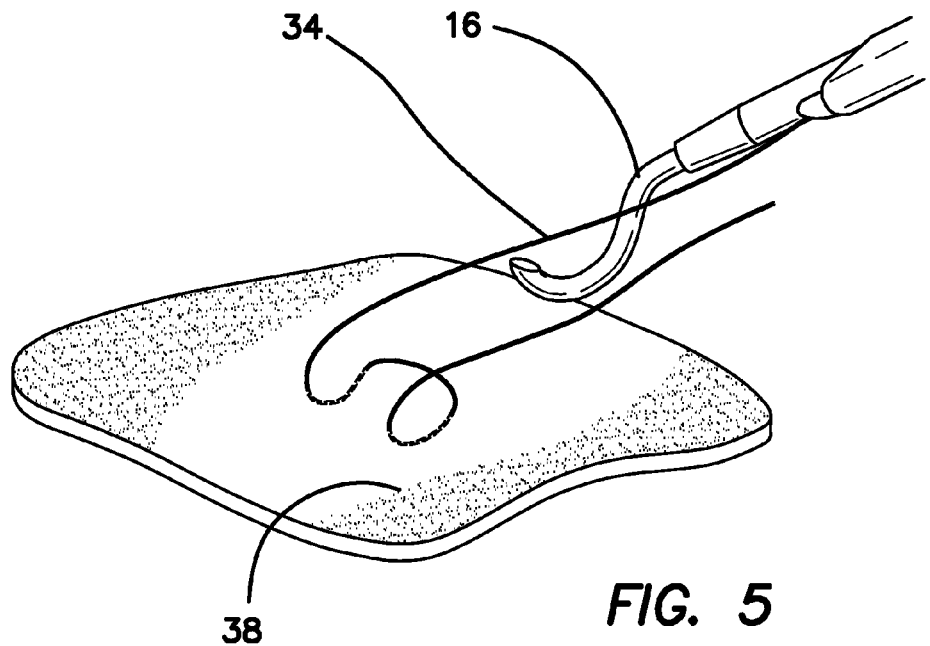
FIG. 5 is an isometric view similar to FIGS. 2-4, wherein the needle has been removed from the tissue after the second suture pass.

Once the straight needle is advanced, by operating the straight needle slider 20, moving it distally along a slot 42 in the handle 12 (FIGS. 1 and 10), the suture 34 is passed between the two needles by operating the suture slider 22 on the handle 12. The straight needle 18 is retracted, and the curved needle 16 is pulled back through the tissue 38, bringing the suture 34 with it (FIG. 4). The result, at this point, as shown in FIG. 4, after one suture pass, is a simple stitch. If this simple stitch is adequate, in the practitioner's judgment, the practitioner may remove the device from the procedural site, and secure the suture and tissue in place. However, if a mattress stitch or additional pleats are desired, the suture may be passed again. The same procedure is repeated. The practitioner pierces the tissue with the curved needle 16, advances the straight needle 18, and passes the suture 34 between them. The second time, this suture is passed from the curved needle to the straight needle. The straight needle is retracted, bringing the suture with it, and the curved needle is pulled out of the tissue. At this point, as shown in FIG. 5, a mattress stitch has been created in the tissue 38.

If desired, the practitioner may continue to pass suture through the tissue to create more pleats. When finished, the device 10 is removed from the joint space, and the suture is anchored by tying a knot or by securing it to a suture anchor.

FIG. 6 is a detailed view of the suture needle 24. The suture needle is attached to one end of the suture 34, and is the portion passed between the curved and straight needles. The collars 28 on each end of the wire 26 provide a feature with which to secure the suture needle inside the curved and straight needles. The suture 34 may be attached to the coil 32 in many different ways. These ways may include, without limitation, compression between the coil and the wire, woven around the coil (one or more times), looped around the coil and knotted, etc. the coil 32 may also slide along the length of the wire inside the collars. This allows for a shorter length of suture to be pulled into the curved and straight needles, when the suture needle is passed between them. This reduces the risk of suture tangling and suture wear (on the edges of the needles).

FIGS. 7-9 illustrate detailed sequential views of the curved and straight needles described above, and the mechanism used to transfer the suture needle from one to the other.

FIG. 7 shows the device prior to passing the suture needle 24. The straight needle 18 has been advanced distally to meet up with the tip of the curved needle 16, as is also illustrated in FIG. 3. The distal advancement of the straight needle is achieved through actuation of the straight needle slider 20 on the handle 12. The needle grasper 36 is disposed within a lumen 44 within the straight needle 18, and has grasper jaws 46 at its distal end, which are movable between an open and closed position, and are resiliently biased to the open position. When the device 10 is supplied to the practitioner, the needle grasper 36 is pre-loaded into the needle 18, with the jaws 46 being closed around the proximal end of the suture needle 24, as shown in FIG. 7. The opening in the jaws 46 is too small to allow the collar 28 to pull out when the jaws are closed. The lumen 44 has a sufficiently small inner diameter so that it fits closely around the needle grasper to keep the jaws 46 closed.

A second needle grasper 48 is positioned within a lumen 49 in the curved needle 16. This needle grasper 48 also has a pair of grasper jaws 50 disposed on its distal end, which are also movable between an open and closed position, and are also resiliently biased to the open position. The jaws 50 are located within a larger diameter portion of the lumen 49, which permits the jaws 50 to spring open, as shown. The suture 34 passes out of the end of the straight needle 18, from the coil 32, and out of the joint space.

FIG. 8 shows the state of the device 10 as the suture needle 24 is passing through the tissue. At this point, the needle grasper 36 is still securing the suture needle. The other end of the suture needle has entered the jaws 50 of the second needle grasper 48 in the curved needle 16. As the needle grasper 36 in the straight needle 18 advances to the left (and pushes the suture needle with it), the second needle grasper 48 in the curved needle is pushed to the right, as shown, and into a smaller diameter portion of the lumen 49. This forces the jaws 50 into their closed position, thus closing them down around the suture needle and securing the distal end of the suture needle. As the needle grasper 36 continues to move distally, the jaws 46 enter a larger diameter section of the lumen 44 of the straight needle 18. Since the jaws 46 are biased to the open position, they spring open, thus releasing the proximal end of the suture needle.

Once the needle grasper 36 in the straight needle releases the suture needle 24, the second needle grasper 48 is pulled to the right. The suture slider 22 on the handle 12 is utilized to move the suture graspers 36 and 48. The movement of the second needle grasper 48 proximally (to the right) pulls the suture needle through the tissue and into the curved needle. The coil 32 slides down the suture needle until it comes into contact with the collar 28, at which point it is pulled through the tissue, bringing the suture 34 with it. FIG. 9 shows the suture needle 24 after it has passed through the tissue 38. The next step is to retract the straight needle, using the straight needle slider 20, and to remove the device 10 from the procedural site or to pass suture again to create a more complex stitch, as discussed above in connection with FIGS. 4 and 5. If the suture is passed again, to create a more complex stitch, the suture needle will be passed the second time in the opposite direction, from the curved needle 16 to the straight needle 18.

Figure 10:
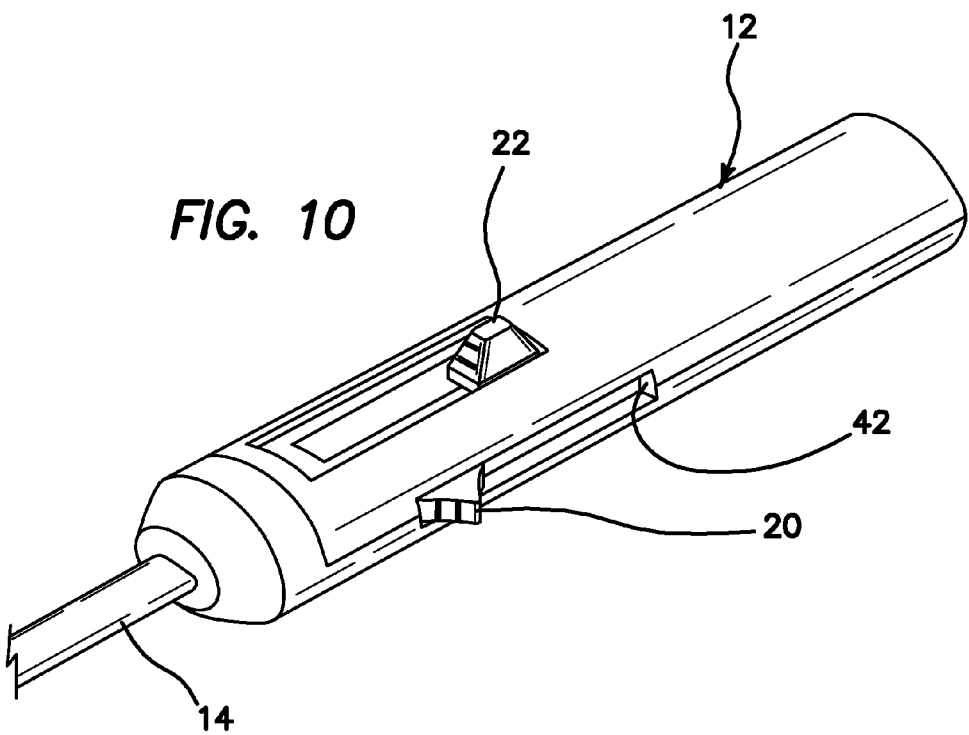
FIG. 10 is an isometric view of the device handle of the invention.

FIG. 10 illustrates the handle 12 of the inventive device 10, in an enlarged format. Although there are many versions of the mechanism and interface that could be used to operate the device 10, this approach is simple and user friendly. As shown, the straight needle slider 20 slides axially between proximal and distal positions within the slot 42, to advance and retract the straight needle 18. When the straight needle slider 20 is moved to the distal position to advance the needle 18, it can be locked in place. This keeps the needles in or clamped around the tissue 38 and holds the straight needle 18 in place as the suture is passed. The slider 20 may be locked in place with a snap feature, utilized a release button to allow it to retract, rotate, or detent into a locked position, or any other number of methods. The suture slider 22 is moved axially along a slot 54 to transfer the suture needle between the curved and straight needles, in both directions.

There are many potential ways to attach suture to the suture needle. The coil 32, shown, is a simple method which can slide along the flexible wire 26 as the suture needle is passed through the tissue. However, the coil could be replaced by a number of other designs, such as a solid tube with a hole for tying the suture, a piece of heat shrink tubing which compresses the suture over the flexible wire, etc. The coil could alternatively be eliminated and the flexible wire pierced through the braided suture. Also, due to size constraints, the suture may be replaced by monofilament suture, suture smaller than #2, or metal wire. The other end of this wire would be attached to the suture that stays in the tissue (usually #2 high strength suture).

As shown in FIGS. 7-9, the needle graspers 36 and 48 open and closed based upon their location with the straight and curved needles, respectively. When they are in the larger diameter section, the jaws spring open. When they are in the smaller diameter section, the jaws close around the suture needle. This timing could be altered by making the smaller diameter section a separate tube which slides inside the respective straight and curved needles. This feature would allow the needle graspers to be opened or closed at any point during their travel, and thus could be used to change the timing of operation during the suture passing procedure.

It is to be understood that the invention as shown and described herein is potentially applicable to many different types of procedures requiring suture passing and the creation of one or more stitches in tissue. All of the terms used herein are descriptive rather than limiting, and many changes, modifications, and substitutions may be made by one having ordinary skill in the art without departing from the spirit and scope of the invention, which is to be limited only in accordance with the following claims.

What is claimed is:

1. A method of repairing soft tissue, comprising:
   introducing an instrument having a curved needle and a movable straight needle, each extending distally from a proximal actuator portion, into an operative site;
   piercing tissue to be sutured with a distal end of the curved needle;
   advancing the straight needle until a distal end thereof lines up with and meets the distal end of the curved needle:
   passing a suture needle disposed in one of said curved and movable straight needles into the other one of said needles, wherein the suture needle is initially clamped on one end by a grasper disposed in said one of said curved and movable straight needles, and the passing step comprises moving the grasper distally to push the suture needle out of said one of said curved and movable straight needles, and into the other of said curved and movable straight needles, the passing step further comprising releasing the one end of the suture needle from the grasper and clamping the other end of the suture needle using a second grasper disposed in the other of said curved and movable straight needles;
   retracting the movable straight needle proximally; and
   pulling the curved needle back through the tissue, thereby creating a stitch of suture in the tissue.

2. The method as recited in claim 1, wherein suture is pre-loaded into the straight needle.

3. The method as recited in claim 2, wherein, during the piercing step, the curved needle is disposed in a suture exit location where one end of the suture emerges.

4. The method as recited in claim 3, wherein, during the piercing step, the instrument is manipulated so that the location of suture exit is aligned with the straight needle.

5. The method as recited in claim 1, wherein the straight needle stops during the advancing step at the point wherein the distal end thereof lines up with and meets the distal end of the curved needle.

6. The method as recited in claim 1, wherein the step of advancing the straight needle is performed by operating a straight needle slider, which moves along a slot in a handle of the instrument.

7. The method as recited in claim 1, wherein the passing step comprises passing the suture on the suture needle from one of the curved and movable straight needles into the other one of said needles by operating a suture slider on a handle of the instrument.

8. The method as recited in claim 1, wherein each of said steps are repeated one or more additional times in order to create a corresponding number of additional stitches of suture.

\* \* \* \* \*